United States Patent [19]
Bertaud et al.

[11] Patent Number: 5,112,309
[45] Date of Patent: May 12, 1992

[54] SENSOR DELIVERY DEVICE

[75] Inventors: Francois X. Bertaud, Libertyville; Richard W. Grabenkort, Barrington, both of Ill.; Beverly A. Magrane, Redmond, Wash.; Gerald G. Vurek, Mountain View, Calif.

[73] Assignee: Abbott Laboratories, Abbott Park, Ill.

[21] Appl. No.: 558,035

[22] Filed: Jul. 25, 1990

[51] Int. Cl.⁵ .......................... H61M 25/00
[52] U.S. Cl. ...................... 604/171; 604/271; 128/772
[58] Field of Search ............ 604/21, 164, 171, 194, 604/198, 159, 284, 901, 271, 280; 128/634, 637, 656, 657, 658, 771, 772

[56] References Cited

U.S. PATENT DOCUMENTS

| | | | |
|---|---|---|---|
| 3,000,380 | 9/1961 | Doherty | 128/214 |
| 3,669,099 | 6/1972 | Silverman | 128/2 M |
| 3,682,173 | 8/1972 | Center | 604/159 |
| 3,894,540 | 7/1975 | Bonner, Jr. | 128/349 R |
| 3,911,927 | 10/1975 | Rich et al. | 128/349 R |
| 4,068,659 | 1/1978 | Moorehead | 128/214.4 |
| 4,311,139 | 1/1982 | Smith | 604/164 |
| 4,464,171 | 8/1984 | Garwin | 604/164 |
| 4,650,462 | 3/1987 | DeSatnick et al. | 128/51 |
| 4,652,256 | 3/1987 | Vaillancourt | 604/164 |
| 4,785,814 | 11/1988 | Kane | 128/634 |
| 4,795,434 | 1/1989 | Kujawski | 604/159 |
| 4,906,232 | 3/1990 | Reynolds | 604/171 |
| 4,994,641 | 2/1991 | Dombrowski et al. | 604/164 |

Primary Examiner—Stephen C. Pellegrino
Assistant Examiner—Steven J. Shumaker
Attorney, Agent, or Firm—Christensen, O'Connor, Johnson & Kindness

[57] ABSTRACT

A device for storing and delivering a sensor through a catheter. A sensor delivery device (10, 10') includes an elongate tube (20), which is attached to a rigid housing (22,22'). A sensor (12), stored within a sterile environment comprising an interior of the sensor delivery device, has an attached signal line (16) that extends along the longitudinal axis of the delivery device and through its proximal end. The proximal end is open when the sensor is in its stored position. An eversible sheath (34) extends between the rigid housing and the signal line, sealingly separating the sterile environment (48) in which the sensor is stored from the open end of the rigid housing. To use the sensor, the signal line is moved into the rigid housing, causing the eversible sheath to turn inside out as the sensor is advanced through the catheter into its use position. The projection afforded by the eversible sheath permits the sensor to be withdrawn through the catheter and then reinsertd without introducing contamination. A probe stop (54) abuts an inner surface of a catheter fitting (17), precisely controlling the distance that the sensor extends beyond a distal end of the catheter.

11 Claims, 6 Drawing Sheets

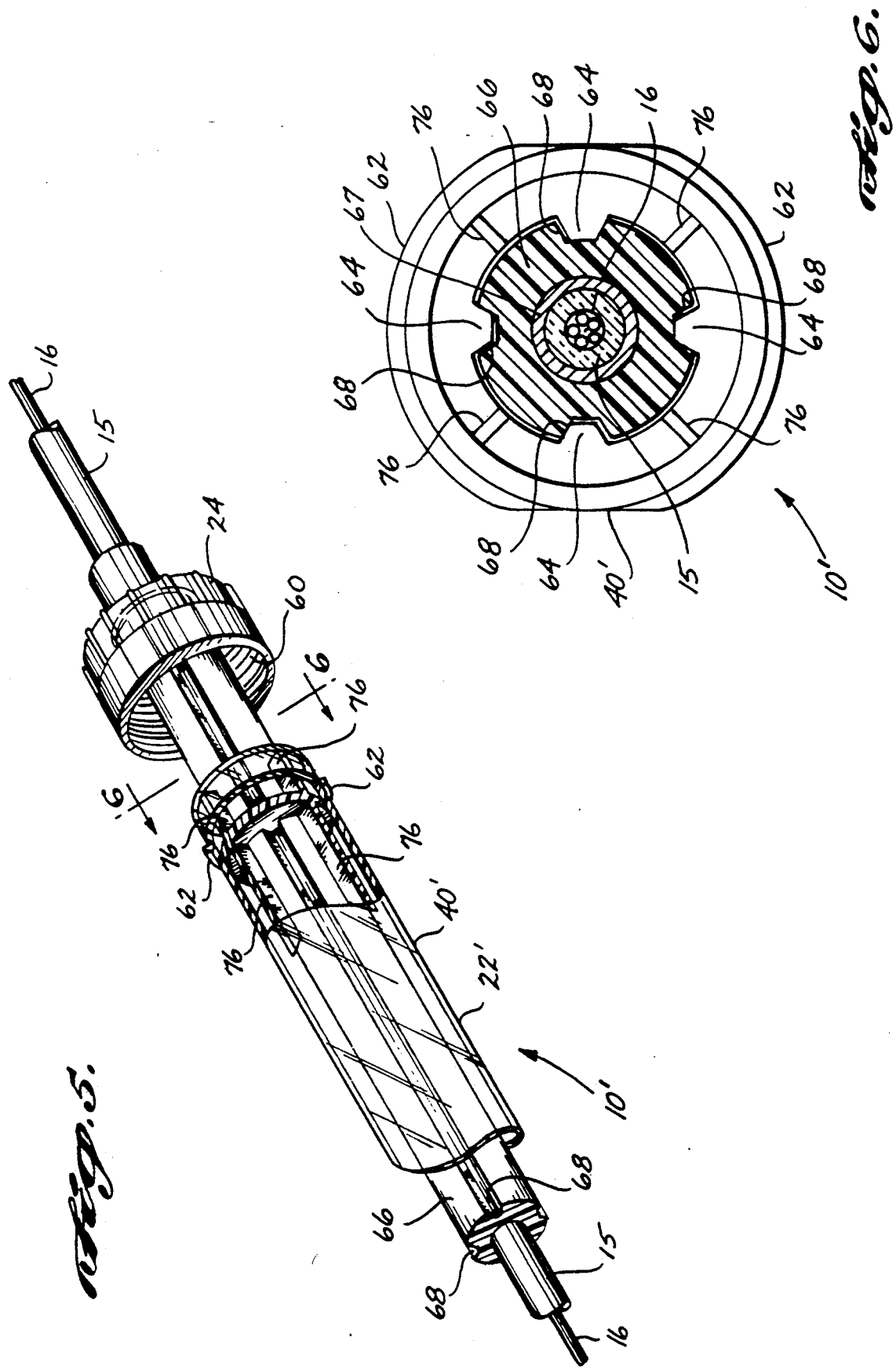

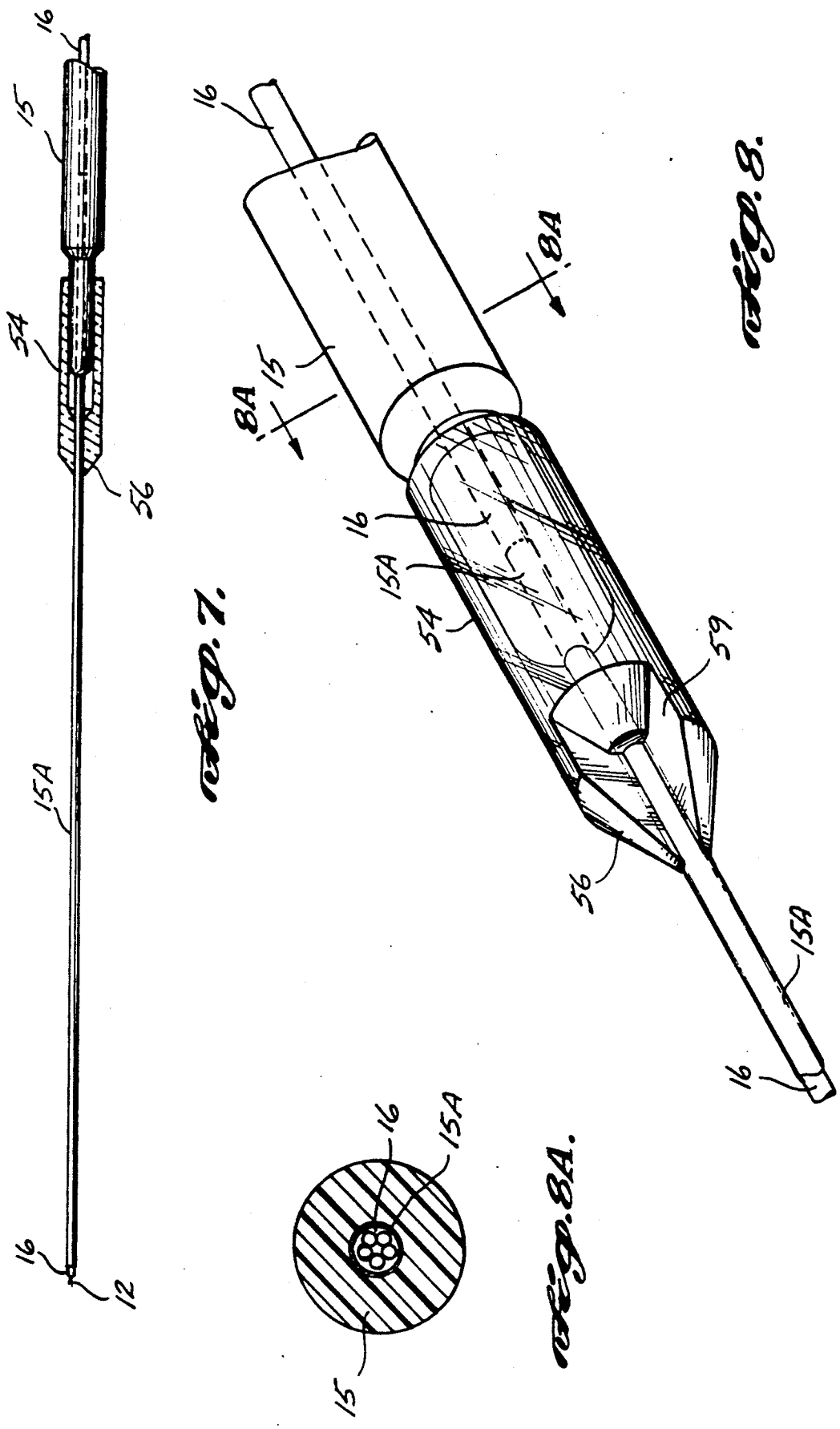

SENSOR DELIVERY DEVICE

TECHNICAL FIELD

This invention generally pertains to a device used for advancing a probe into an attached tube, and more specifically, to a device for delivering a medical sensor through an intravascular catheter.

BACKGROUND OF THE INVENTION

Development of specialized in vivo sensors associated with monitoring conditions related to a patient's circulatory system has created the need for a device that can be readily attached to a preplaced catheter and used to advance a sensor into the patient's vascular system. The sensor delivery device must also satisfy other requirements. Prior to use of the delivery device, the sensor must be sterile and it must be maintained free from outside bacteriological contamination. The sensor may be stored in the delivery device prior to use, or withdrawn from the catheter into the delivery device during its use. A contaminant-free environment inside the portion of the delivery device to which the sensor is exposed should thus be maintained as the sensor is advanced through the catheter, to permit withdrawal of the sensor for subsequent reuse with the same patient. Bodily fluid leakage from the catheter through the delivery device must be avoided; yet, the delivery device should permit sampling of blood pressure, withdrawal of blood samples, and introduction of medicinal fluids into the circulatory system of the patient.

Furthermore, the delivery device should control the position of the sensor relative to the distal end of the catheter to ensure that the sensor is properly exposed to a patient's bloodstream but does not extend so far beyond the end of the catheter that it is no longer protected by an anticoagulant heparin solution flowing through the catheter. For example, fiber-optic blood gas sensors used to monitor $PCO_2$ and $PO_2$ are designed to extend into the bloodstream only a few hundredths of an inch beyond a distal end of the catheter. Thus, it is critically important that the delivery device properly position the sensor with respect to the distal end of the catheter.

SUMMARY OF THE INVENTION

In accordance with this invention, an apparatus is defined for maintaining a medical device in a sterile environment and delivering the sensor and an attached signal line through a catheter. The apparatus includes an elongate tubular housing having a proximal end and a distal end, the distal end being adapted for attachment to the catheter. The medical device is disposed within a sterile environment comprising an interior of the tubular housing, and is movable from that position through the catheter, after the catheter is attached to the tubular housing. A flexible sheath disposed within the interior of the tubular housing sealingly extends between the tubular housing and the signal line. The flexible sheath sealingly encloses the sensor within the sterile environment, and as the medical device is advanced from the interior of the tubular housing into the catheter, the flexible sheath collapses so that the sterile environment is maintained. In one preferred embodiment, the flexible sheath everts (i.e., turns inside-out). The flexible sheath prevents outside contamination of the sterile environment that might otherwise result due to exposure of the interior to a nonsterile portion of the signal line as the line is advanced into the tubular housing.

A sliding seal is disposed between the distal and proximal ends of the tubular housing, in close sliding contact with the line. The sliding seal prevents fluid from flowing around the line from the distal end of the housing into the proximal end, but permits the line to slide longitudinally through the sliding seal.

A passage in fluid communication with the interior of the tubular housing is provided for infusing and withdrawing fluid. The fluid freely flows through the catheter, around and past the medical device and its attached signal line. Preferably, the passage is disposed within a sidewall of the tubular housing, between the distal end of the tubular housing and the sliding seal. In addition, the apparatus includes a sterilant inlet opening into the interior of the tubular housing to provide fluid communication with the interior. The sterilant inlet opening enables a sterilant gas to be infused into the interior and is covered with a microbial filter through which air passes freely as the medical device is advanced and withdrawn through the catheter.

Also included and emphasized as an important aspect of the invention is a stop disposed on the line at a predefined distance from the medical device. The stop abuts against an inner surface of a fitting on the catheter to limit advancement of the medical device so that it extends only a predefined distance beyond a distal end of the catheter. At least one passage is formed in the stop to permit fluid to flow past the stop when it is abutting the inner surface of the catheter fitting.

Means are also provided for preventing rotation of the signal line relative to the tubular housing, thereby preventing twisting of the flexible sheath that might otherwise occur. The means for preventing rotation comprise a ridge and a mating groove that extend between an inner surface of the tubular housing and an outer surface of the signal line, generally in alignment with its longitudinal axis. The ridge engages the groove to prevent rotation of the signal line, yet allows longitudinal movement of the signal line relative to the tubular housing.

BRIEF DESCRIPTION OF THE DRAWINGS

FIG. 5 is a cutaway view of a proximal end of the delivery device showing the means for centering and a ridge and groove configuration for preventing rotation of the signal line;

FIG. 6 is a cross-sectional view, taken along section line 6—6 of FIG. 5;

FIG. 7 is a cross-sectional view of a portion of the signal line with a stop that controls advancement of the sensor through the catheter;

FIG. 8 is a greatly enlarged view of the stop on a portion of the signal line; and FIG. 8A is a cross-sectional view of a portion of the signal line, taken along section line 8A—8A of FIG. 8.

DESCRIPTION OF THE PREFERRED EMBODIMENTS

Figure 1:
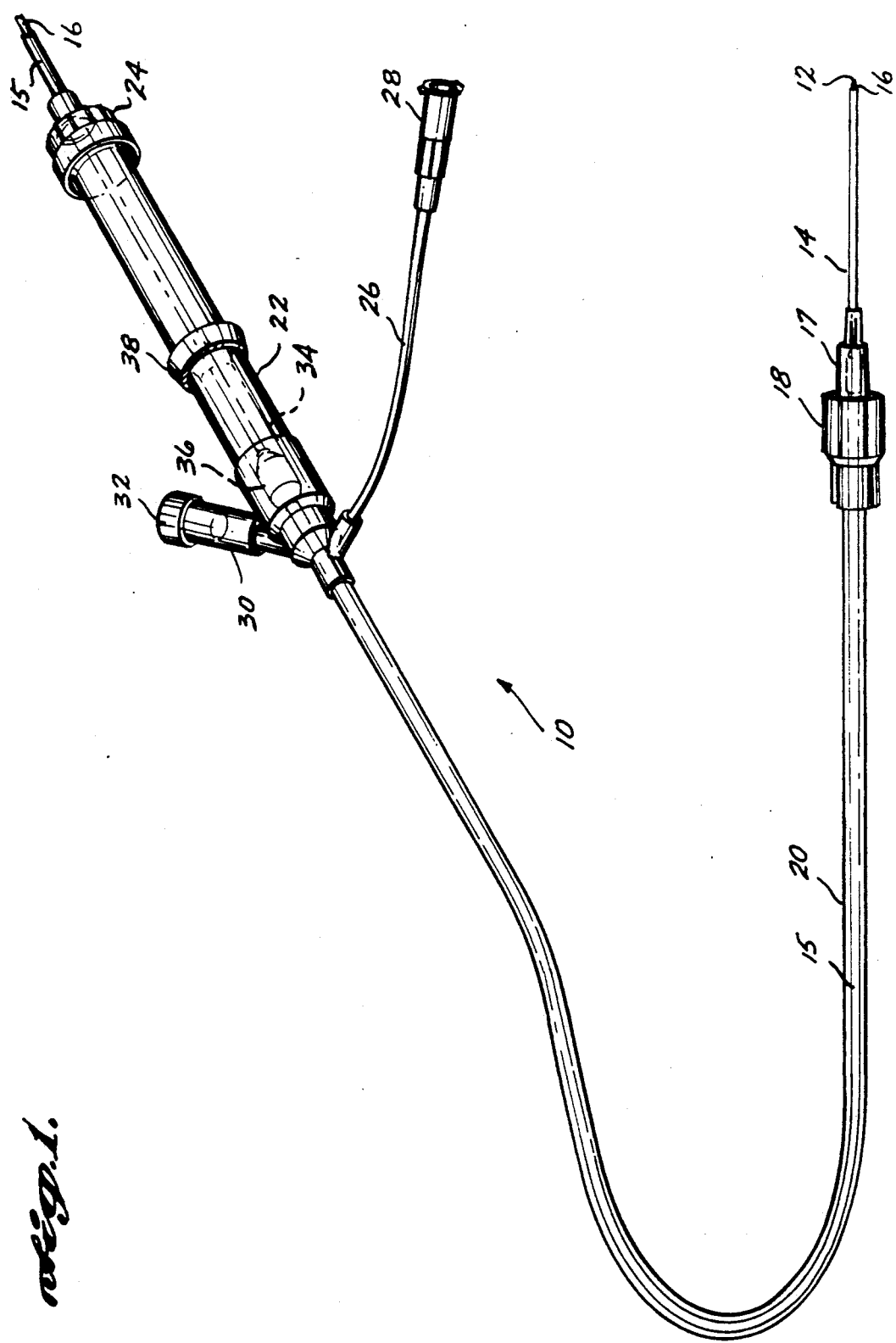
FIG. 1 is an isometric view of a first preferred embodiment of the sensor delivery device, attached to a catheter (not part of the delivery device)
Figure 2:
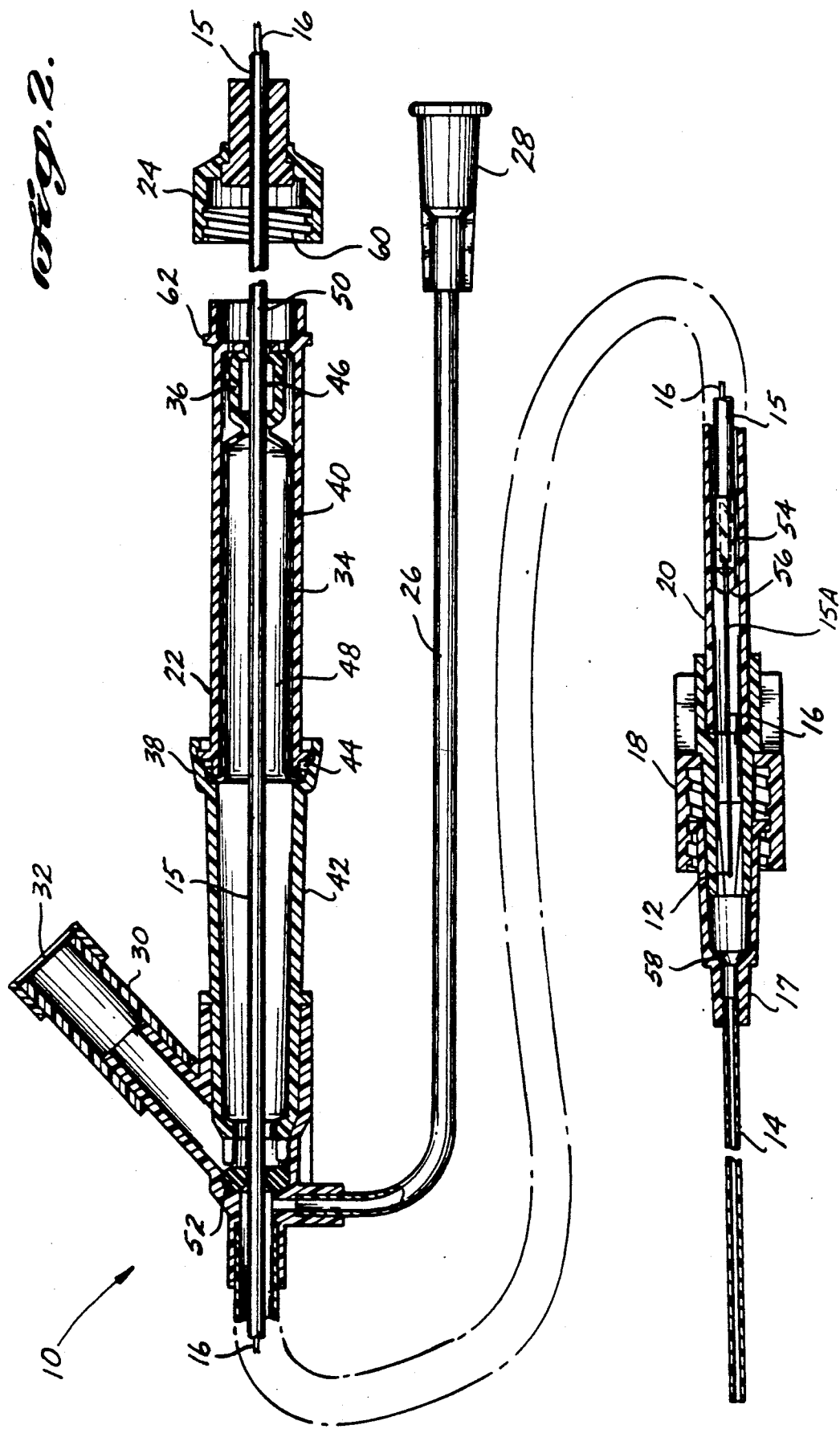
FIG. 2 is a cross-sectional view of the delivery device shown in FIG. 1, wherein a sensor with an attached signal line is shown in a storage position within the delivery device, after attachment to the catheter and prior to use.
Figure 3:
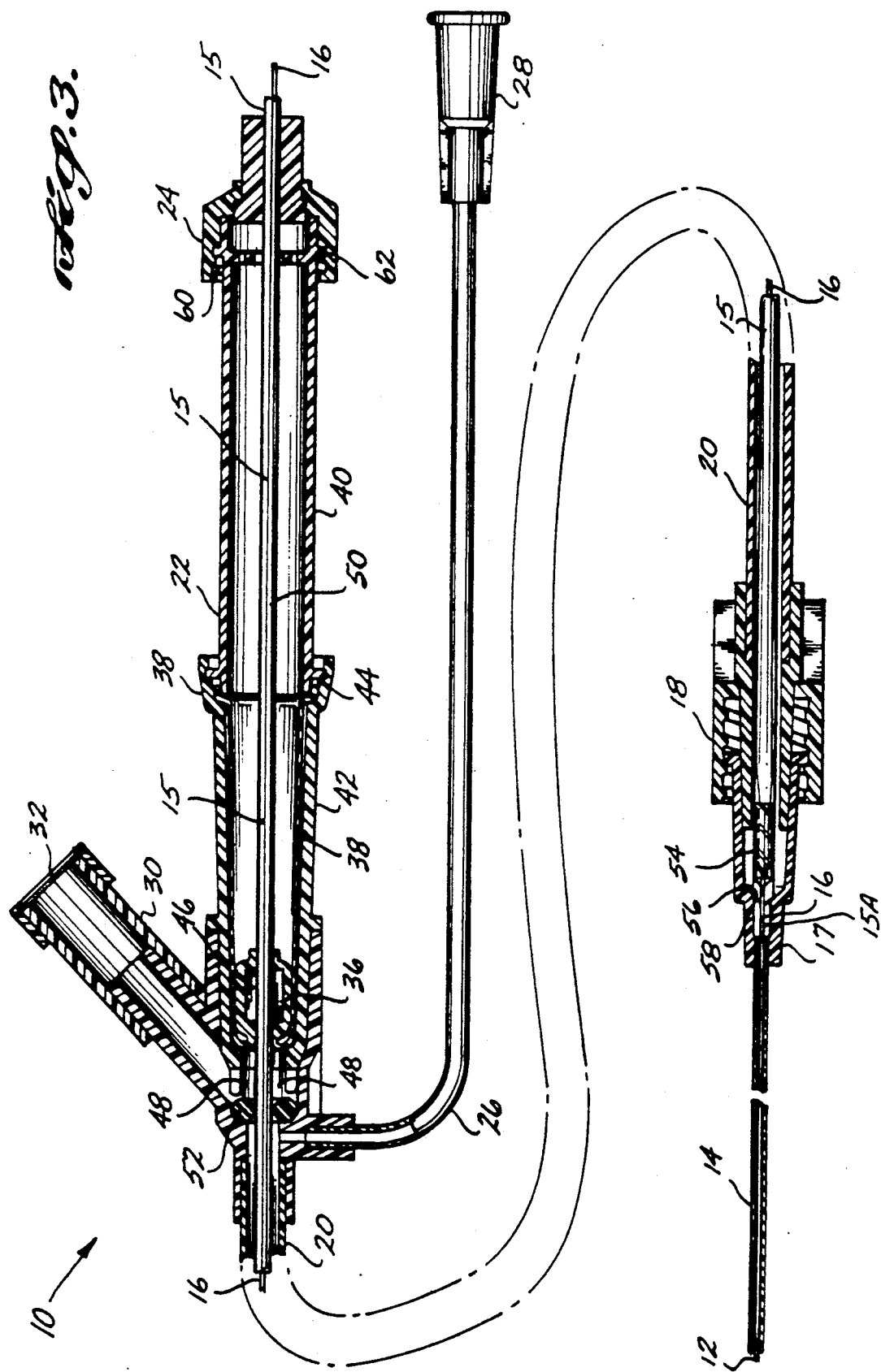
FIG. 3 is a cross-sectional view of the first embodiment of the delivery device shown in FIG. 1, illustrating the disposition of the sensor after it is advanced through the catheter into a position of use.

With reference to FIGS. 1-3, a first embodiment of the sensor delivery device is shown, generally identified at reference numeral 10. Sensor delivery device 10 can be used for storing a sensor 12 in a sterile environment and for controlling the position of the sensor in respect to a distal end of a catheter 14. Prior to use of sensor 12, sensor delivery device 10 is connected to catheter 14, which may be preinserted within a patient's artery or vein (not shown). Sensor 12 may, for example, comprise a fiber optic probe for monitoring blood gases in vivo. However, other types of medical devices introduced through a catheter could also be used in connection with the present invention. Sensor delivery device 10 is adapted to connect to catheter 14 by provision of an internally threaded connector 18, which is disposed on a distal end of an elongate flexible tube 20. A proximal end of catheter 14 includes an externally threaded, generally cylindrical, nozzle-shaped hub or fitting 17, which engages connector 18. After fitting 17 is connected to delivery device 10 via connector 18, sensor 12 is advanced through catheter 14 from a sterile environment within elongate tube 20, until the sensor extends into the patient's bloodstream, controllably positioned by the delivery device to a point that is a few hundredths of an inch beyond the distal end of catheter 14. An important aspect of the present invention is its ability to precisely position sensor 12 with respect to the distal end of catheter 14.

Elongate tube 20 is attached to a rigid housing 22. A signal line 16 attached to sensor 12 extends along a longitudinal axis of both elongate tube 20 and rigid housing 22, through a cap 24. Cap 24 is rotatably attached to the signal line at a predetermined proximal distance above sensor 12; the cap is secured to a proximal end of rigid housing 22 when sensor 12 is advanced from its storage position through catheter 14, to its position of use. Signals (light and/or electrical) produced by sensor 12 are conveyed through signal line 16 to and from appropriate connected instrumentation (not shown). Signal line 16 comprises a plurality of optical fibers and electrical conductors (not separately shown) that are enclosed within a protective plastic sleeve 15. A very small diameter (0.017 inches in the preferred embodiment) tube 15A covers the distal end of signal line 16, except where sensor 12 is exposed. Tube 15A is separate from but joined to plastic sleeve 15 and protects and stiffens the portion of signal line 16 that moves within catheter 14. Tube 15A is shown more clearly in FIGS. 7, 8, and 8A.

As shown in FIG. 2, the diameter of sleeve 15 is less than the internal diameter of elongate tube 20. Similarly, the diameter of tube 15A is less than the internal diameter of catheter 14. Therefore, the space surrounding sleeve 15 and tube 15A, i.e., the annular space between sleeve 15 and the inner surfaces of elongate tube 20 and the annular space between tube 15A and catheter 14, provides a path for fluid communication with the patient's bloodstream for monitoring blood pressure, withdrawal of blood samples, or injection of medicinal fluids while sensor 12 is in use. Fluids are either withdrawn from or injected into the bloodstream through a fluid access tube 26, which extends laterally through a sidewall of elongate tube 20, from a portion of rigid housing 22 that is attached to the elongate tube. Fluid access tube 26 includes a connector 28 on its distal end, for connection to appropriate monitoring equipment and/or fluid injection/withdrawal apparatus (none shown). The preferred embodiment also includes a sterilant inlet 30 that extends at an acute angle outwardly from rigid housing 22, adjacent the point where it connects to elongate tube 20. A microporous filter screen 32 having a maximum pore size of approximately 0.2 microns is fitted into the open end of sterilant inlet 30. Due to the small pore size, microporous filter screen 32 functions as a microbial filter and excludes bacteriological contamination from entering rigid housing 22 when air is drawn into or expelled from the rigid housing as the sensor is moved.

Inside rigid housing 22, in the preferred form of the delivery device, an eversible sheath 34 extends between a bonded joint 38 and signal line 16. Bonded joint 38 circumferentially surrounds rigid housing 22 at about its midpoint. The end of the eversible sheath attached to sleeve 15 includes a compression ring 36 that is elastically biased to seal around an annular fitting 46 bonded to sleeve 15. Eversible sheath 34 preferably comprises an elastomeric membrane, formed of rubber or other suitable elastomeric material. The eversible sheath functions as a contamination barrier, protecting the sterile environment within elongate tube 20 (in which the sensor is stored prior to use) from contamination by exposure to externally introduced bacteria as sensor 12 is advanced through catheter 14 from its retracted position into its position of use. Further, if it becomes necessary to withdraw sensor 12 back through catheter 14 into its retracted position, contamination of the sensor due to exposure of an interior part of rigid housing 22 to nonsterile portions of signal line 16 is thus prevented. A non-eversible sheath (not shown) that simply collapses as sensor 12 is either advanced or withdrawn from catheter 14 might alternatively be used in place of eversible sheath 34. However, the non-eversible sheath would not permit the extent of travel of sensor 12 provided by eversible sheath 34 and would be more prone to damage or perforation during repeated use of the sensor delivery device.

In FIGS. 2 and 3, the disposition of sensor 12 and eversible sheath 34 are illustrated respectively prior to and after advancement of the sensor through catheter 14. With reference to FIG. 2, sensor 12 is shown in its retracted position, i.e., disposed within the distal end of elongate tube 20. Prior to advancement of sensor 12, eversible sheath 34 extends from bonded joint 38 toward the proximal end of rigid housing 22. A ring 44 formed at one end of eversible sheath 34 around its circumference, is captured between an upper portion 40 and a lower portion 42 of rigid housing 22, where they are connected at bonded joint 38. Compression ring 36 at the opposite end of eversible sheath 34 is bonded to annular fitting 46.

Prior to being packaged for shipment to an end user, sensor delivery device 10 is subjected to a sterilizing procedure which may include exposure to ethylene oxide gas. The ethylene oxide gas is drawn into the interior of rigid housing 22, through microporous filter screen 32, which covers the outer end of sterilant inlet 30. The gas produces a sterile environment 48 around the portion of signal line 16 that extends into elongate tube 20 of sensor delivery device 10. Ethylene oxide gas is also drawn into the interior of elongate tube 20 through both connector 18 and fluid access tube 26. Alternative means may be used to sterilize the interior of rigid housing 22 and elongate tube 20.

An O-ring sliding seal 52 is disposed between the end of rigid housing 22 that connects to elongate tube 20 and fluid access tube 26. O-ring sliding seal 52 is sized so that its inner diameter is slightly smaller than the diameter of sleeve 15, thereby preventing fluid flowing from elongate tube 20 into the interior of rigid housing 22. However, sleeve 15 slides easily through O-ring sliding seal 52 as sensor 12 and signal line 16 are advanced through catheter 14.

As illustrated in FIG. 3, signal line 16 has been advanced into the interior of rigid housing 22 sufficiently so that threads 60, which are formed on an interior surface of cap 24, can engage a matching threaded ridge 62 that is formed on the outer surface of rigid housing 22, adjacent its proximal end. When a user advances signal line 16 into rigid housing 22, along its longitudinal axis, the signal line moves the attached sensor forward through catheter 14, until a probe stop 54 on sleeve 15 prevents further movement of the sensor, as explained below. At this point, sensor 12 is exposed a predefined distance at the distal end of catheter 14. Advancement of signal line 16 in this fashion also causes eversible sheath 34 to turn inside out. Eversible sheath 34 prevents contamination of the interior of rigid housing 22 distal of bonded joint 38 that would otherwise occur, due to exposure of the interior to a nonsterile portion 50 of signal line 16.

If it becomes necessary to withdraw sensor 12 from catheter 14, for example, to flush the sensor to wash away any thrombi formed thereon, sensor 12 can subsequently be readvanced into the patient's vascular system without concern that the sensor was exposed to contamination by being withdrawn into the interior of rigid housing 22. As sensor 12 and signal line 16 are advanced and withdrawn through catheter 14, microporous filter screen 32 allows air to flow freely in and out of the interior of rigid housing 22, due to displacement by eversible sheath 34, thereby preventing O-ring sliding seal 52 and the eversible sheath from being subjected to any significant differential pressure in respect to atmospheric pressure.

To prevent overtravel of sensor 12 through catheter 14 and control its extension from the catheter, probe stop 54 is bonded to sleeve 15 on signal line 16 at a predefined precise distance proximally behind the sensor. The placement of probe stop 54 at a proper position on signal line 16 is critical in this application and should be accomplished within a tolerance of ±0.005 inches, with the aid of a microscope. In other applications of the invention, the tolerance for positioning the probe stop may be different. Probe stop 54, which is shown in greater detail in FIGS. 7 and 8, is slid along tube 15A and sleeve 15 to the predetermined position, which can vary as a function of the length of catheter 14, before being bonded in place, and is thus adapted to adjust the position of sensor 12 with respect to the distal end of catheters of different length when the sensor is fully advanced through the catheter. Alternatively, the disposition of sensor 12 can be controlled in respect to the position of the probe stop. A shoulder 56 on the forward or distal end of probe stop 54 contacts an abutting surface 58 formed at a point where the internal diameter of a generally cylindrical fitting 17 on catheter 14 necks down. Shoulder 56 is tapered to a conical shape that matches the shape of abutting surface 58 and includes a plurality of longitudinal grooves 59 that enable fluid flow past the shoulder when it is seated against the abutting surface.

The position of probe stop 54 on signal line 16 controls the distance that sensor 12 extends beyond the distal end of catheter 14 to a predefined range (about ±0.02" in the preferred embodiment). Referring to FIG. 3, cap 24 is positioned on signal line 16 at a slightly greater distance behind probe stop 54 than the distance between abutting shoulder 56 and the proximal end of rigid housing 22 so that an excessive length of signal line 16 is advanced into the rigid housing when the cap is secured thereto. The stiffness of sleeve 15 preloads probe stop 54 against abutting surface 58 at all times, even when elongate tube 20 is bent into a curve, due to the added length of signal line 16 that is forced into the rigid housing distal of the cap.

Figure 4:
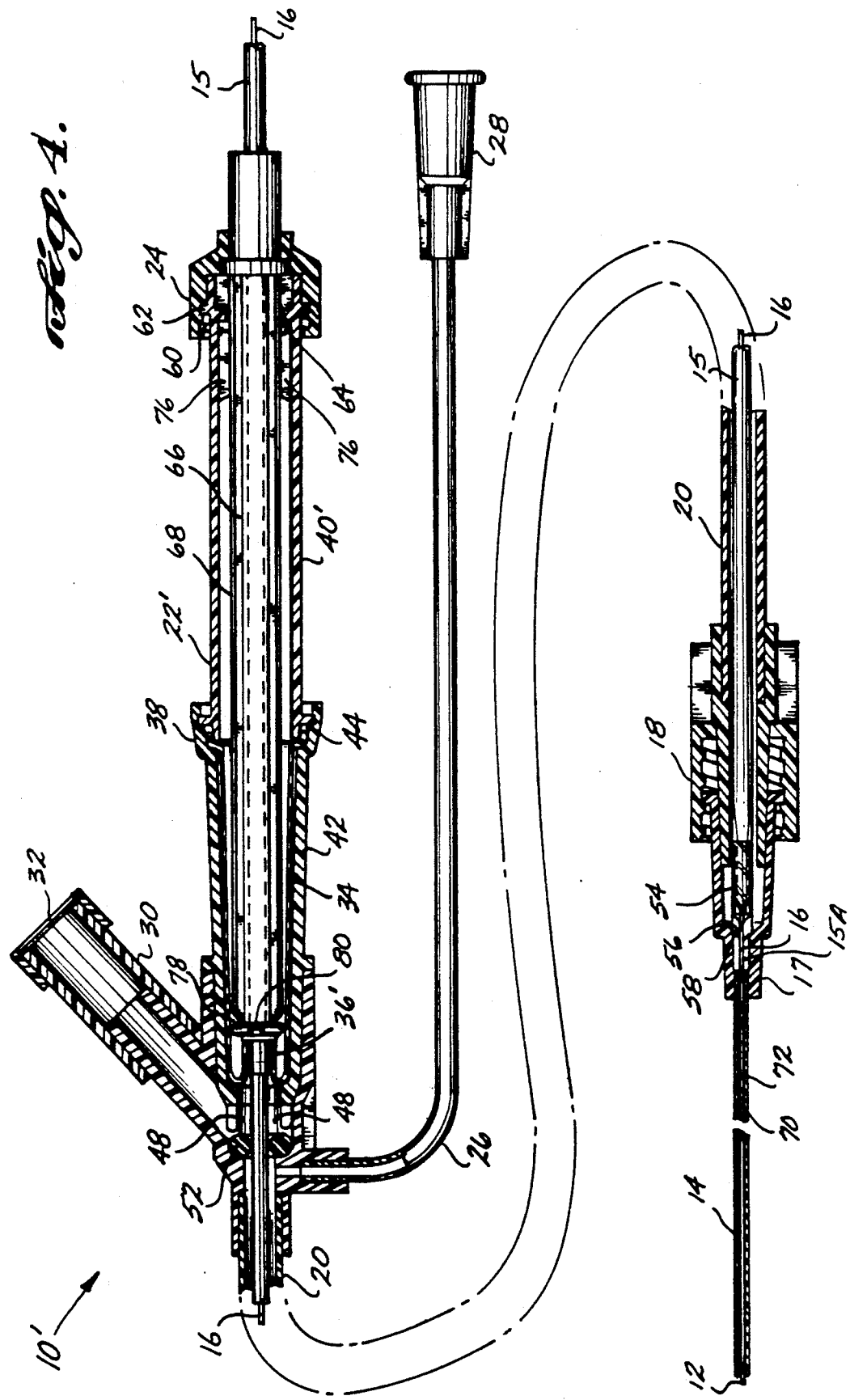
FIG. 4 is a cross-sectional view of a second embodiment of the sensor delivery device, wherein the sensor is in the position of use, the second embodiment including means to prevent rotation of the signal line and means to center the line within the delivery device.

Turning now to FIG. 4, a second preferred embodiment of the sensor delivery device is illustrated generally at reference numeral 10'. Sensor delivery device 10' is substantially the same as the first embodiment, except for certain additions, which are described below. The same reference numerals are applied to each of the elements comprising sensor delivery device 10' as applied in respect to sensor delivery device 10—at least to the elements that are unchanged in function and form. Elements having a different but similar function and/or form are identified using the same numerals, but include a prime notation.

Sensor delivery device 10' includes several performance enhancing features omitted in the first preferred embodiment of the device. For example, rotation of sleeve 15 as it and signal line 16 are advanced or withdrawn from the rigid housing can cause twisting of eversible sheath 34 in sensor delivery device 10. To prevent twisting of an eversible sheath 34' in sensor delivery device 10', an indexed elongate traveler 66 is bonded over the exterior surface of sleeve 15. Traveler 66 is a generally cylindrical molded plastic fitting with a passage through its longitudinal center that extends from a point on sleeve 15 immediately distal cap 24, to a point where a cylindrical end 36' of the eversible sheath is bonded to traveler 66. A steel cannula 67 encloses sleeve 15 within traveler 66 over a portion of its length. Four longitudinal grooves 68 formed in traveler 66 extend in alignment with the longitudinal axis of signal line 16 and are spaced apart around the circumference of the traveler. Four ridges 64 are formed internally within a rigid housing 22', extending radially inwardly from its internal surface adjacent its proximal end. Ridges 64 are shaped and positioned to engage grooves 68, as shown in FIGS. 5 and 6. Engagement of longitudinal grooves 68 by ridges 64 thus prevents rotation of sleeve 15 as well as signal line 16. Complete withdrawal of signal line 16 and traveler 66 from the interior of rigid housing 22' is prevented. As ridges 64 reach the distal ends of longitudinal grooves 68, further retrograde movement is halted where the grooves terminate at the distal end of traveler 66, thereby preventing overtravel that might tear or damage eversible sheath 34'. In addition, traveler 66 provides the user the convenience of a rigid fitting to advance or retract sensor 12 as compared to relying solely on the much more flexible signal line 16.

It will be apparent to those of ordinary skill in the art that the ridges could also be formed on the exterior surface of traveler 66, engaging grooves formed on the interior surface of rigid housing 22'.

Within rigid housing 22', immediately longitudinally adjacent to and angularly spaced apart from ridges 64 are a plurality of additional spacer ridges 76 that extend radially inward from the inner surface in an upper portion 40' of the rigid housing and longitudinally from its open end part way along its length. Spacer ridges 76 maintain traveler 66 concentrically centered within the bore of rigid housing 22', preventing it twisting off the longitudinal axis of the bore. Optionally, an elastomeric ring 78 (shown in FIG. 4) may be seated in an annular groove 80 on traveler 66 to frictionally engage spacer ridges 76 when sensor 12 is fully withdrawn, thereby serving as a detent to hold the sensor in its withdrawn position.

The variations discussed above and other modifications to the preferred embodiments clearly lie within the scope of this invention as defined by the claims that follow. It is not intended that the scope of this invention be in any way limited by the disclosure of the preferred embodiments, but instead that it be determined entirely by reference to these claims.

The embodiments of the invention in which an exclusive property or privilege is claimed are defined as follows:

1. Apparatus for maintaining a medical device in a sterile environment and delivering the medical device and an attached line through a catheter, comprising:
    an elongate tubular housing having a proximal end and a distal end, said proximal end having an opening through which the line extends, said distal end including means for attachment to the catheter, an interior portion of the tubular housing, defining the sterile environment in which the medical device is maintained, the tubular housing including means for moving the medical device therefrom through the catheter after the catheter is attached to the tubular housing; and
    a flexible sheath disposed within the interior of the tubular housing, sealingly attached to the line and to the tubular housing and extending between the tubular housing and the line, thereby sealingly enclosing said medical device within said sterile environment, said flexible sheath collapsing on itself, but continuing to provide a barrier against external contamination of the sterile environment as the medical device is advanced from the interior portion of the tubular housing into the catheter so that the sterile environment is maintained and not contaminated by exposure to a nonsterile portion of the line that is advanced into the tubular housing.

2. The apparatus of claim 1, wherein the flexible sheath everts as the medical device is advanced.

3. The apparatus of claim 1, further comprising a sliding seal disposed between the distal and proximal ends of the tubular housing, in close sliding sealing contact with the line, said sliding seal preventing fluid from flowing around the line from the distal end into the proximal end, but permitting the line to slide longitudinally freely through said sliding seal.

4. The apparatus of claim 3, further comprising a passage in fluid communication with the interior of the tubular housing, said passage comprising means for infusing and withdrawing fluid, said fluid flowing through the catheter, around and past the medical device and its attached line.

5. The apparatus of claim 4, wherein the passage is disposed within a sidewall of the tubular housing, between the distal end and the sliding seal.

6. The apparatus of claim 1, further comprising an aspiration inlet opening into the tubular housing, in fluid communication with the sterile environment in the interior portion.

7. The apparatus of claim 6, wherein the aspiration inlet, which comprises means for enabling a sterilant gas to be infused into the interior prior to use of the apparatus, is closed with a microbial filter through which air freely passes as the medical device is advanced or withdrawn through the catheter.

8. The apparatus of claim 1, wherein a stop is disposed on the line, said stop abutting against an inner surface of a hub on the catheter to limit advancement of the medical device so that it extends only a predefined distance beyond a distal end of the catheter.

9. The apparatus of claim 8, wherein said stop includes at least one passage through which fluid can flow when the stop is abutting the inner surface of said hub.

10. The apparatus of claim 8, further comprising a cap rotatably attached on the line, said cap engaging the proximal end of the tubular housing after the line is advanced sufficiently so that the stop abuts against the inner surface of said hub, an excess length of the line then disposed within the tubular housing acting to bias the stop into abutment with the inner surface of said hub.

11. The apparatus of claim 1, further comprising means for preventing rotation of the line relative to the tubular housing, said means for preventing rotation including a ridge and a mating groove that extend between an inner surface and an outer surface of the signal line, generally in alignment with its longitudinal axis, said ridge engaging the groove to prevent rotation of the line, yet allowing longitudinal movement of the line relative to the tubular housing.

* * * * *